US00PP09810P

United States Patent [19]

VandenBerg

[11] Patent Number: Plant 9,810

[45] Date of Patent: Feb. 25, 1997

[54] CHRYSANTHEMUM PLANT NAMED 'SONATA'

[75] Inventor: Cornelis P. VandenBerg, Salinas, Calif.

[73] Assignee: Yoder Brothers, Inc., Barberton, Ohio

[21] Appl. No.: 547,756

[22] Filed: Oct. 24, 1995

[51] Int. Cl.[6] ..... A01H 5/00

[52] U.S. Cl. ..... Plt./77

[58] Field of Search ..... Plt./76, 77, 78

*Primary Examiner*—Howard J. Locker

*Attorney, Agent, or Firm*—Foley & Lardner

[57] ABSTRACT

A Chrysanthemum plant named Sonata particularly characterized by its flat capitulum form; decorative capitulum type; creamy white ray floret color with a cream center of the flower; diameter across face of capitulum of 70 to 76 mm when fully opened, when grown as a single stem spray cut mum; flowering response in Salinas under normal temperatures is 52 to 57 days after start of short days; flowering response in Bogota, Colombia is 61 to 69 days; plant height is 89 to 107 cm when grown in Salinas with 11 long days prior to start of short days; plant height is 97 to 114 cm when grown in Bogota with 14 to 15 long days prior to start of short days; peduncle length of the first lateral at flowering after removing the apical bud is 8 to 10 cm when grown in Salinas, and 10 to 13 cm when grown in Bogota; peducle length of the fourth lateral at flowering is 10 to 15 cm when grown in Salinas, and 15 to 18 cm when grown in Bogota; excellent tolerance to low night temperatures for bud initiation and flower development; and recommended as a spray cut mum.

3 Drawing Sheets

The present invention comprises a new and distinct cultivar of Chrysanthemum, botanically known as *Dendranthema grandiflora,* and referred to by the cultivar name Sonata.

Sonata, identified as 1221 (90-005002), was originated from a cross made by Cornelis P. VandenBerg in a controlled breeding program in Salinas, Calif. in 1989.

The female parent of Sonata was an unnamed seedling, identified as 1135 (85-248002) and described as a white decorative spray cut mum. The female parent was discarded from all programs in August of 1990.

The male parent of Sonata was an unnamed seedling, identified as 1359 (85-271002) and described as white decorative spray cut mum with many disc florets.

Sonata was discovered and selected as one flowering plant within the progeny of the stated cross by Cornelis P. VandenBerg in April 1991, in a controlled environment in Salinas, Calif.

The first act of asexual reproduction of Sonata was accomplished when vegetative cuttings were taken from the initial selection in June 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Sonata are firmly fixed and are retained through successive generations of asexual reproduction.

Sonata has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low night temperature tolerance was determined in repeated flowerings in Bogota, Colombia, with an average minimum low night temperature inside the greenhouse during our trials ranging as low as 5 to 8 degrees Celsius.

The following traits have been repeatedly observed and are determined to be basic characteristics of Sonata, which, in combination, distinguish this Chrysanthemum as a new and distinct cultivar:

1. Flat capitulum form.
2. Decorative capitulum type.
3. Creamy white ray floret color with a cream center of the flower.
4. Diameter across face of capitulum of 70 to 76 mm when fully opened, when grown as a single stem spray cut mum.
5 Flowering response in Salinas under normal temperatures is 52 to 57 days after start of short days. Flowering response in Bogota, Colombia is 61 to 69 days.
6. Plant height is 89 to 107 cm when grown in Salinas with 11 long days prior to start of short days; plant height is 97 to 114 cm when grown in Bogota with 14 to 15 long days prior to start of short days.
7. Peduncle length of the first lateral at flowering after removing the apical bud is 8 to 10 cm when grown in Salinas, and 10 to 13 cm when grown in Bogota, Peduncle length of the fourth lateral at flowering is 10 to 15 cm when grown in Salinas, and 15 to 18 cm when grown in Bogota.
8. Excellent tolerance to low night temperatures for bud initiation and flower development.
9. Recommended as a spry cut mum.

The accompanying photographic drawings show typical inflorescence and leaf characteristics of Sonata, with the colors being as nearly true as possible with illustrations of this type.

Sheet 1 is a color photograph of Sonata grown as a single stem spray cut mum, grown in Salinas, Calif.

Sheet 2 is a black and white photograph of three views of the inflorescence of Sonata.

Sheet 3 is a black and white photograph showing the upper and under sides of the leaves of Sonata at 3 stages of development (mature, intermediate and immature). In sheets 2 and 3 a measuring tape in centimeters has been added.

Of the commercial cultivars known to the inventor, the most similar in comparison to Sonata is the cultivar identified as Polaris, an unpatented but commercial cultivar. Reference is made to attached Chart A, which compares certain characteristics of Sonata with the same characteristics of Polaris. Similar traits are ray floret color and capitulum form and type. Sonata has a more pronounced cream center of the flower than Polaris. Sonata has a smaller diameter of capitulum, a slower flowering response to short days in Salinas, a faster flowering response to short days in Bogota, a shorter plant height and shorter peduncles when compared with Polaris.

In the following description color references are made to The Royal Horticultural Society Colour Chart. The color values were determined on plant material grown as a single stem spray cut mum in Salinas, Calif. on Jul. 3, 1995.

Classification:

*Botanical.*—*Dendranthema grandiflora* cv Sonata.

*Commercial.*—Flat decorative spray cut mum.

INFLORESCENCE

A. Capitulum:

*Form.*—Flat.

*Type.*—Decorative.

*Diameter across face.*—70 to 76 mm when fully opened.

B. Corolla of ray florets:

*Color (general tonality from a distance of three meters).*—Creamy white with cream center of the flower.

*Color (upper surface).*—155A, center of flower 8C.

*Color (under surface).*—155A.

*Shape.*—Straight, cross section concave rounded petal tip.

C. Corolla of disc florets:

*Color (mature).*—Closest to 15A.

*Color (immature).*—Closest to 144B.

D. Reproductive organs:

*Androecium.*—Present on disc florets only; no pollen.

*Gynoecium.*—Present on both ray and disc florets.

PLANT

A. General appearance:

*Height.*—89 to 107 cm when grown in Salinas with 11 long days prior to start of short days; 97 to 114 cm when grown in Bogota with 14 to 15 long days prior to start of short days.

B. Foliage:

*Color (upper surface).*—147A.

*Color (under surface).*—147B

*Shape.*—Deeply lobed, serrated.

CHART A

COMPARISON OF SONATA AND POLARIS

| CHARACTERISTIC | SONATA | POLARIS |
|---|---|---|
| Ray floret color | Creamy white | Creamy white |
| Capitulum form | Flat | Flat |
| Capitulum type | Decorative | Decorative |
| Diameter across face of capitulum | 70 to 76 mm | 76 to 83 mm |
| Flowering response | | |
| in Salinas | 52 to 57 days | 51 to 53 days |
| in Bogota | 61 to 69 days | 69 to 73 days |
| Plant height with | | |
| 6–11 long days Salinas | 89 to 107 cm | 94 to 104 cm |
| 14–15 long days Bogota | 97 to 114 cm | 107 to 127 cm |
| Peduncle length | | |
| 1st lateral, Salinas | 8 to 10 cm | 10 to 14 cm |
| 4th lateral Salinas | 10 to 15 cm | 18 to 20 cm |
| 1st lateral, Bogota | 10 to 13 cm | 15 to 18 cm |
| 4th lateral, Bogota | 15 to 18 cm | 20 to 23 cm |

COMPARISONS MADE OF PLANTS GROWN AS SINGLE STEM SPRAY CUT MUMS IN SALINAS, CALIFORNIA AND IN BOGOTA, COLUMBIA

What is claimed is:

1. A new and distinct Chrysanthemum plant named Sonata, as described and illustrated.

* * * * *

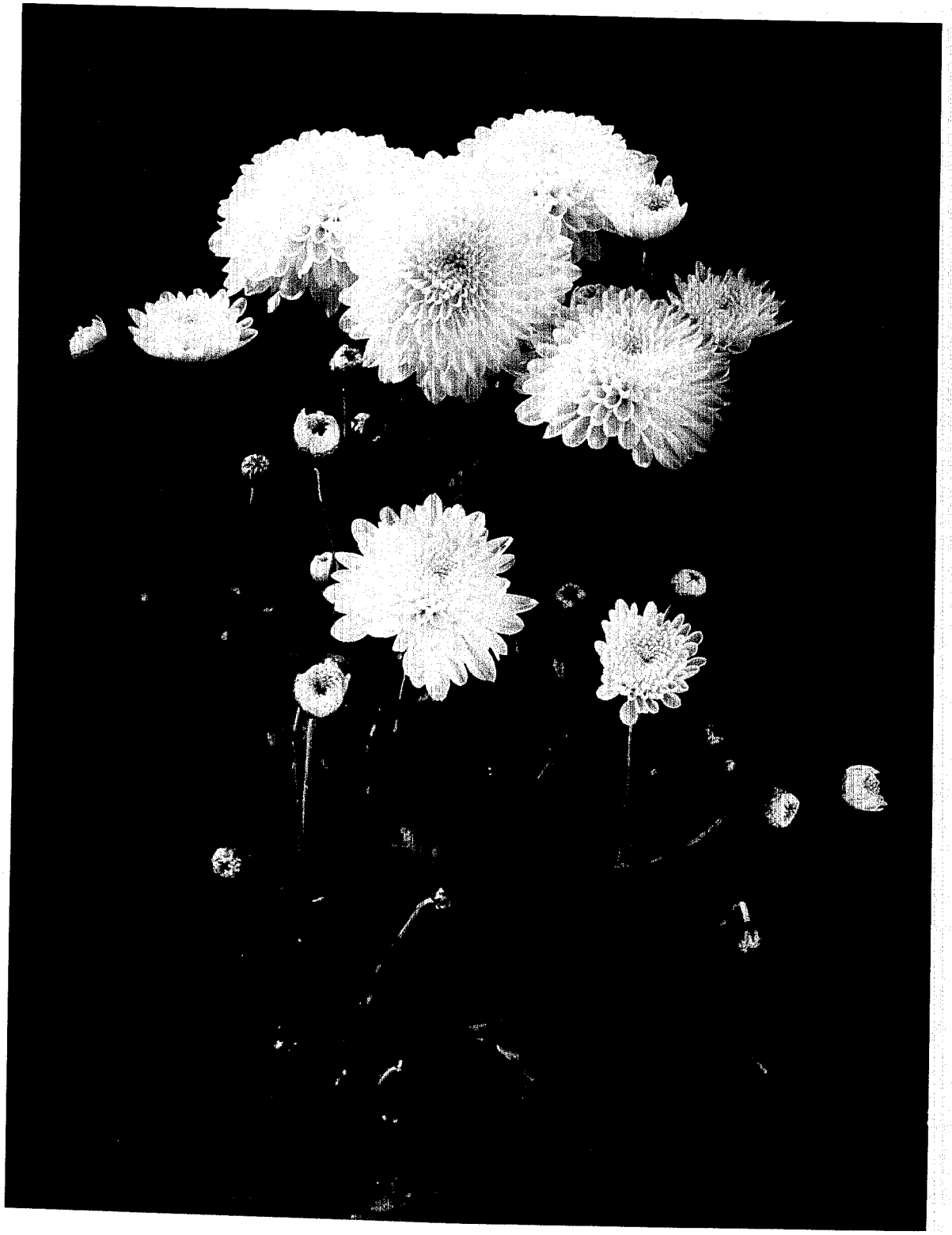

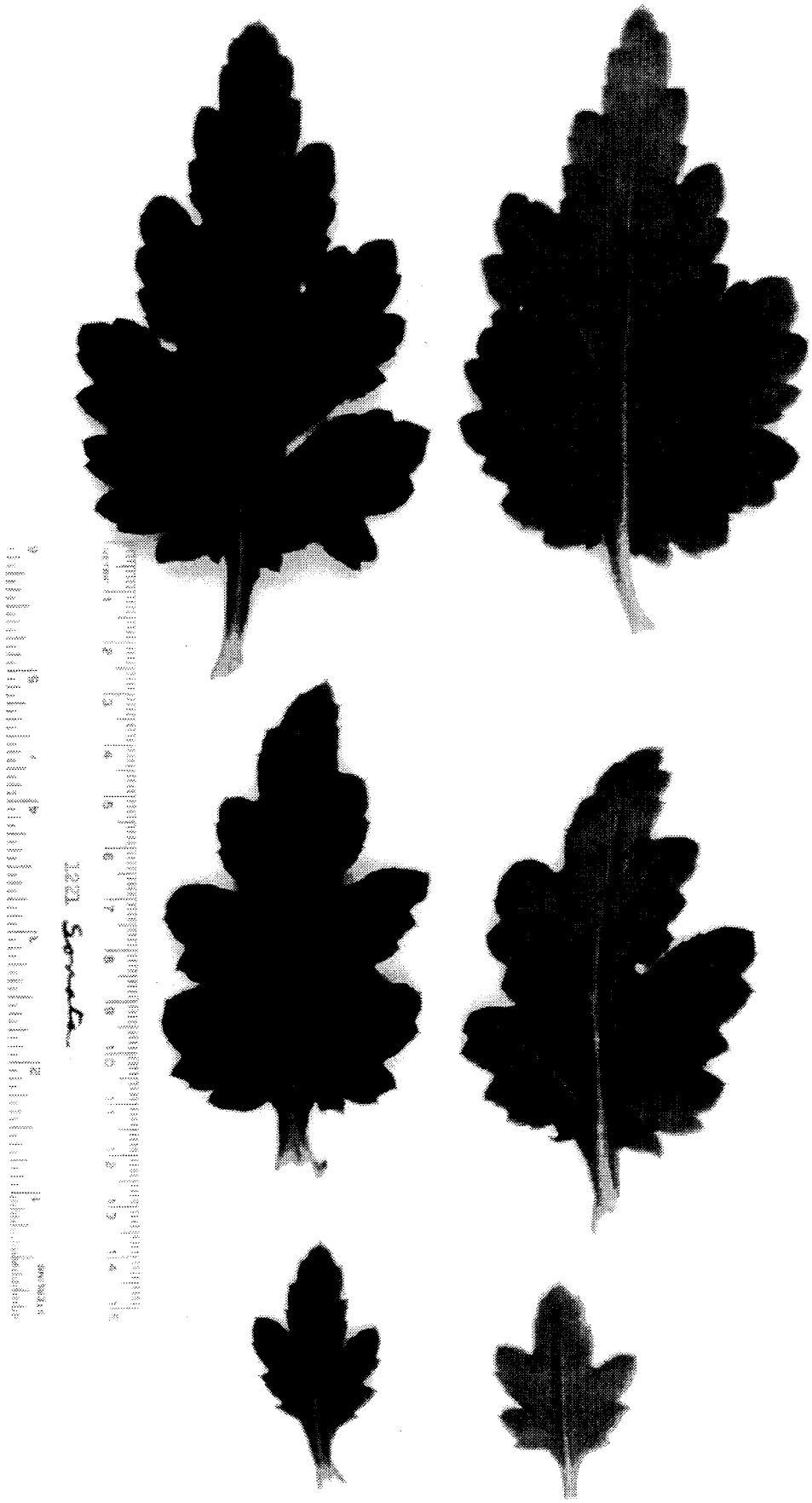

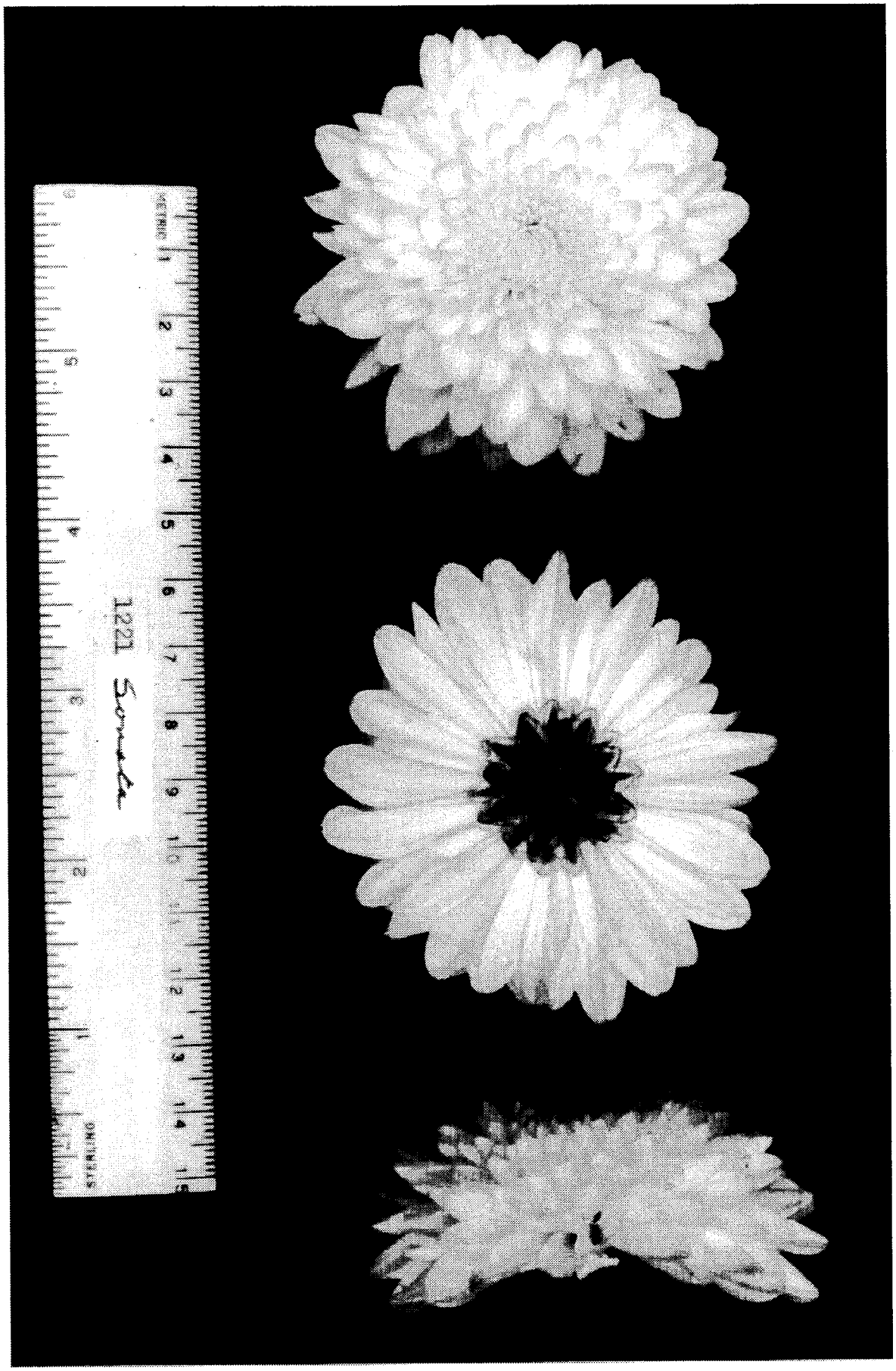
1221 Sonata